United States Patent
Yang et al.

(10) Patent No.: US 10,406,023 B2
(45) Date of Patent: Sep. 10, 2019

(54) SMART COOLING PASTE

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Shengji Yang, Beijing (CN); Xue Dong, Beijing (CN); Haisheng Wang, Beijing (CN); Xiaochuan Chen, Beijing (CN); Jiantao Liu, Beijing (CN); Jingbo Xu, Beijing (CN); Yingzi Wang, Beijing (CN); Yingming Liu, Beijing (CN); Weijie Zhao, Beijing (CN); Changfeng Li, Beijing (CN); Xiaoliang Ding, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

(*) Notice: Subject to any disclaimer, the term of this patent is extended or adjusted under 35 U.S.C. 154(b) by 225 days.

(21) Appl. No.: 15/124,667

(22) PCT Filed: Nov. 10, 2015

(86) PCT No.: PCT/CN2015/094204
§ 371 (c)(1),
(2) Date: Sep. 8, 2016

(87) PCT Pub. No.: WO2016/188044
PCT Pub. Date: Dec. 1, 2016

(65) Prior Publication Data
US 2017/0112661 A1  Apr. 27, 2017

(30) Foreign Application Priority Data
May 28, 2015 (CN) .......................... 2015 1 0283537

(51) Int. Cl.
A61F 7/02 (2006.01)
A61B 5/01 (2006.01)
(Continued)

(52) U.S. Cl.
CPC .................. *A61F 7/02* (2013.01); *A61B 5/01* (2013.01); *A61B 5/6833* (2013.01); *A61B 5/742* (2013.01);
(Continued)

(58) Field of Classification Search
CPC ...... A61F 2007/0007; A61F 2007/0093; A61F 2007/0095; A61F 2007/0096; A61F 7/02;
(Continued)

(56) References Cited

U.S. PATENT DOCUMENTS 5,643,336 A * 7/1997 Lopez-Claros ........... A61F 7/02
126/204
8,657,758 B2 * 2/2014 Lia .......................... A61B 5/01
600/549

(Continued)

FOREIGN PATENT DOCUMENTS

CN      1273819 A    11/2000
CN    201342006 Y    11/2009
(Continued)

OTHER PUBLICATIONS

Office Action in Chinese Application No. 201510283537.8 dated Dec. 27, 2016, with English translation. 14 pages.
(Continued)

Primary Examiner — Kaitlyn E Smith
Assistant Examiner — Bradford C. Blaise
(74) Attorney, Agent, or Firm — Womble Bond Dickinson (US) LLP

(57) ABSTRACT

A smart cooling system is disclosed. The smart cooling system includes: a cooling system body and a temperature
(Continued)

sensing module, a touch display module and a control module. The cooling system body includes a carrier and a gel layer located on the carrier. The temperature sensing module, the touch display module and the control module are fixed on the carrier. A sensing surface of the temperature sensing module and a surface of the gel layer away from the carrier are in a same plane, for sensing temperature of forehead. The control module is used for obtaining a sensed temperature and transmitting the sensed temperature to the touch display module. A screen of the touch display module is located on a surface of the carrier away from the gel layer.

8 Claims, 3 Drawing Sheets

(51) Int. Cl.
 *A61B 5/00* (2006.01)
 *A61F 7/00* (2006.01)
(52) U.S. Cl.
 CPC ...... *A61B 5/746* (2013.01); *A61F 2007/0007* (2013.01); *A61F 2007/0068* (2013.01); *A61F 2007/0093* (2013.01); *A61F 2007/0095* (2013.01); *A61F 2007/0096* (2013.01); *A61F 2007/026* (2013.01); *A61F 2007/0219* (2013.01); *A61F 2007/0225* (2013.01); *A61F 2007/0226* (2013.01); *A61F 2007/0228* (2013.01); *A61F 2007/0244* (2013.01); *A61F 2007/0261* (2013.01); *A61F 2007/0277* (2013.01)
(58) Field of Classification Search
 CPC ...... A61F 2007/0215; A61F 2007/0219; A61F 2007/0225; A61F 2007/0226; A61F 2007/0228; A61F 2007/0244; A61F 2007/0277; A61F 2007/0282; A61F 2007/022; A61F 2007/0268; A61F 2007/0269; A61F 2007/0271; A61F 2007/0273
 See application file for complete search history.

(56) References Cited

U.S. PATENT DOCUMENTS

| | | | | |
|---|---|---|---|---|
| 9,693,689 | B2* | 7/2017 | Gannon | A61B 5/0008 |
| 9,782,082 | B2* | 10/2017 | Gannon | A61B 5/002 |
| 2002/0017997 | A1* | 2/2002 | Felkowitz | G01K 1/024 |
| | | | | 340/573.1 |
| 2004/0059400 | A1* | 3/2004 | Lin | A61F 7/007 |
| | | | | 607/109 |
| 2004/0215098 | A1* | 10/2004 | Barton | A61B 5/0008 |
| | | | | 600/549 |
| 2005/0280531 | A1* | 12/2005 | Fadem | A61B 5/0006 |
| | | | | 340/539.12 |
| 2006/0139165 | A1 | 6/2006 | Bader | |
| 2008/0091089 | A1* | 4/2008 | Guillory | A61B 5/0478 |
| | | | | 600/301 |
| 2008/0137709 | A1* | 6/2008 | Quinn | A01K 29/005 |
| | | | | 374/121 |
| 2010/0137953 | A1* | 6/2010 | Stein | A41D 31/00 |
| | | | | 607/112 |
| 2012/0109232 | A1* | 5/2012 | Mohn | A61F 7/02 |
| | | | | 607/3 |
| 2013/0245546 | A1* | 9/2013 | Hayn | A61F 7/02 |
| | | | | 604/66 |
| 2013/0331914 | A1* | 12/2013 | Lee | A61F 7/007 |
| | | | | 607/96 |
| 2014/0303698 | A1* | 10/2014 | Benyaminpour | A61F 7/02 |
| | | | | 607/107 |
| 2014/0352325 | A1* | 12/2014 | Brown | F25B 21/02 |
| | | | | 62/3.2 |
| 2015/0297397 | A1* | 10/2015 | Rand | A61F 7/106 |
| | | | | 607/110 |
| 2016/0354232 | A1* | 12/2016 | Rozental | A61F 7/10 |
| 2017/0246031 | A1* | 8/2017 | Benyaminpour | B60R 21/235 |

FOREIGN PATENT DOCUMENTS

| | | |
|---|---|---|
| CN | 102599894 A | 7/2012 |
| CN | 202761729 U | 3/2013 |
| CN | 202761825 U | 3/2013 |
| CN | 203354742 U | 12/2013 |
| CN | 103816003 A | 5/2014 |
| CN | 203677362 U | 7/2014 |
| CN | 203852467 U | 10/2014 |
| CN | 104251737 A | 12/2014 |
| CN | 204121234 U | 1/2015 |
| CN | 204218891 U | 3/2015 |
| CN | 204319035 U | 5/2015 |
| CN | 104887384 A | 9/2015 |
| CN | 204671362 U | 9/2015 |
| EP | 1 085 409 A2 | 3/2001 |
| JP | 2004236970 A | 8/2004 |

OTHER PUBLICATIONS

International Search Report and Written Opinion in PCT/CN2015/094204 dated Jan. 20, 2016, with English translation. 16 pages.

Office Action in Chinese Application No. 201510283537.8 dated Jun. 27, 2016, with English translation. 10 pages.

Office Action in Chinese Application No. 201510283537.8 dated Jun. 12, 2017, with English translation.

* cited by examiner

SMART COOLING PASTE

The present application is the U.S. national phase entry of PCT/CN2015/094204, with an international filing date of Nov. 10, 2015, which claims the benefit of Chinese Patent Application No. 201510283537.8, filed on May 28, 2015, the entire disclosure of which is incorporated herein by reference.

TECHNICAL FIELD

The present disclosure relates to the field of medical technology, particularly to a smart cooling system.

BACKGROUND

Fever, especially fever in children, is a common frequently-occurring disease, which may influence children's health if it is not treated in time. The existing anti-fever medicines have high side effects and are oral medicines mostly, which is not favorable for children to use.

The cooling system is a new technology for emergency cooling of a high fever that has been developed in recent years. As shown in FIG. 1, the cooling system comprises three layers, which are respectively anti-adhesion layer 101, a gel layer 102 and a protective layer 103. The principle of the cooling system is locking the liquid state water through the polymer gel in the gel layer 102, absorbing the heat on the surface of the forehead and converting it into vapor, so as to reduce the temperature of the head of the children locally.

However, in the process of using the cooling system, the effect of the cooling system cannot be learned. Only after the body temperature of the children is measured by using the thermometer can it be learned whether the cooling system plays the function of cooling.

SUMMARY

Embodiments of the present disclosure provides a smart cooling system, the effect of which can be learned at any time in the process of use.

In order to achieve the above object, embodiments of the present disclosure adopt the following technical solutions:

A smart cooling system is provided, comprising: a cooling system body and a temperature sensing module, a touch display module and a control module. The cooling system body comprises a carrier and a gel layer located on the carrier. The temperature sensing module, the touch display module and the control module are fixed on the carrier. A sensing surface of the temperature sensing module and a surface of the gel layer away from the carrier are in a same plane, for sensing temperature of forehead. The control module is used for obtaining a sensed temperature and transmitting the sensed temperature to the touch display module. A screen of the touch display module is located on a surface of the carrier away from the gel layer.

In an embodiment, the smart cooling system further comprises a storage module. The storage module is used for storing the sensed temperature obtained from the temperature sensing module by the control module.

In an embodiment, the touch display module is further used for displaying operation control information and obtaining a user instruction based on the operation control information. The operation control information comprises identifications for indicating real time temperature information and temperature curve information. The control module is used for obtaining the real time temperature information or the temperature curve information based on the user instruction and transmitting them to the touch display module.

In an embodiment, when the user instruction indicates that the user selects the real time temperature information, the control module is used for obtaining the sensed temperature from the temperature sensing module and transmitting the sensed temperature to the touch display module; and when the user instruction indicates that the user selects the temperature curve information, the control module is used for obtaining temperatures within a preset time from the storage module, deriving a temperature variation curve based on the temperatures within the preset time, and transmitting the temperature variation curve to the touch display module.

In an embodiment, the smart cooling system further comprises an alarm module. When the control module determines based on the sensed temperature obtained from the temperature sensing module that the sensed temperature is higher than a preset temperature value, the control module sends an alarm signal to the alarm module so as to enable the alarm module to give an alarm in the form of sound or light.

In an embodiment, the smart cooling system further comprises a communication module. The control module transmits the sensed temperature to a mobile terminal through the communication module.

In an embodiment, the smart cooling system further comprises at least one drugstore device fixed on the carrier, in which freshener is stored. The control module is further used for controlling the drugstore device to inject a preset amount of freshener into the gel layer based on the sensed temperature.

In an embodiment, the drugstore device has an opening that can be closed. The control module controls the opening to be open based on the sensed temperature so as to enable the freshener in the drugstore device to be injected into the gel layer, and closes the opening when a preset time arrives.

In an embodiment, the number of the drugstore devices is two, and the two drugstore devices are arranged at two opposite ends of the carrier in a detachable manner respectively and are in contact with the gel layer.

In an embodiment, the smart cooling system further comprises a first elastic band and a second elastic band arranged at two opposite ends of the carrier respectively. The first elastic band and the second elastic band are connected in a detachable manner.

Embodiments of the present disclosure provide a smart cooling system. In the process of using the smart cooling system, the temperature of the forehead of the patient can be obtained in real time through a temperature sensing module. The temperature can be displayed on a screen of a touch display module through a control module, so as to learn the body temperature of the patient in the process of using the smart cooling system, thereby being capable of learning the effect of the cooling system at any time.

BRIEF DESCRIPTION OF THE DRAWINGS

In order to explain the embodiments of the present disclosure or the technical solutions in the prior art more clearly, the drawings to be used in the description of the embodiments or the prior art will be introduced briefly hereinafter. Apparently, the drawings described below are only some embodiments of the present disclosure. The ordinary skilled person in the art can obtain other drawings based on these drawings without paying any creative work.

DETAILED DESCRIPTION

Reference Signs

101—anti-adhesion layer; 102—gel layer; 103—protective layer; 20—carrier; 30—temperature sensing module; 40—touch display module; 50—control module; 60—storage module; 70—alarm module; 80—communication module; 90—drugstore module; 91—opening; 111—first elastic band; 112—second elastic band.

Next, the technical solutions in the embodiments of the present disclosure will be described clearly and completely with reference to the drawings in the embodiments of the present disclosure. Apparently, the embodiments described are only a part of rather than all of the embodiments of the present disclosure. Based on the described embodiments, all other embodiments obtained by the ordinary skilled person in the art without paying any creative work belong to the protection scope of the present disclosure.

Figure 1:
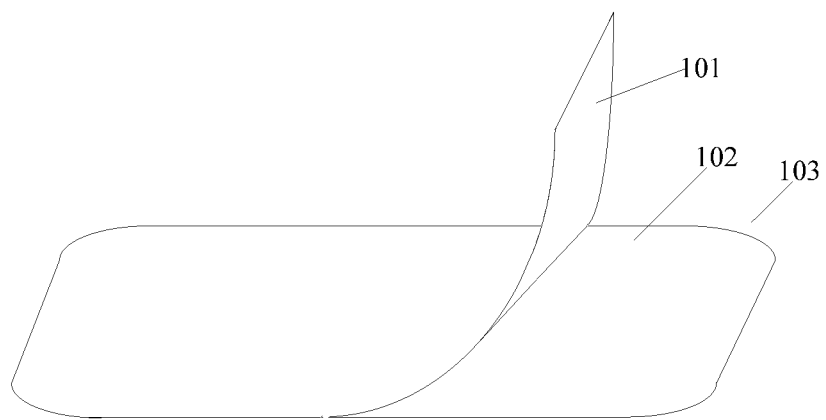
FIG. 1 is a schematic view of a cooling system of the prior art.
Figure 2:
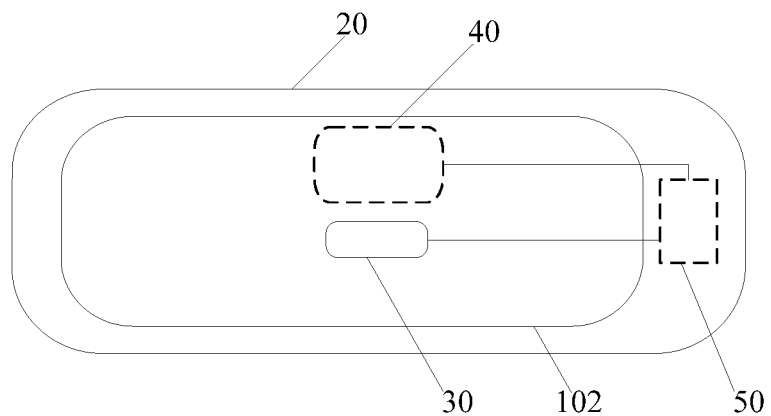
FIG. 2 is a vertical schematic view of back of a smart cooling system according to embodiments of the present disclosure.
Figure 3:
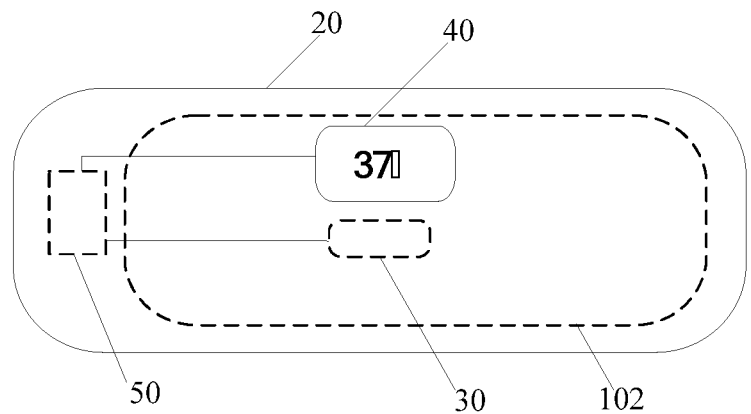
FIG. 3 is a vertical schematic view of front of a smart cooling system according to embodiments of the present disclosure.

Embodiments of the present disclosure provide a smart cooling system, as shown in FIG. 2 and FIG. 3. The smart cooling system comprises: a cooling system body and a temperature sensing module 30, a touch display module 40 and a control module 50. The cooling system body comprises a carrier 20 and a gel layer 102 located on the carrier. The temperature sensing module 30, the touch display module 40 and the control module 50 are fixed on the carrier 20. A sensing surface of the temperature sensing module 30 and a surface of the gel layer 102 away from the carrier 20 are in a same plane, for sensing temperature of forehead. The control module 50 is used for obtaining a sensed temperature and transmitting the sensed temperature to the touch display module 40. A screen of the touch display module 40 is located on a surface of the carrier 20 away from the gel layer 102.

The smart cooling system can further comprise an anti-adhesion layer covering the gel layer 102, which can be ripped off in use.

In embodiments of the present disclosure, a side of the cooling system body with the gel layer 102 can be called a back side, and a side of the cooling system body that exposes the screen of the touch display module 40 is called a front side. On the basis of this, the sensing surface of temperature sensing module 30 is located at the back side of the cooling system body.

It should be noted that firstly, the skilled person in the art should know that the gel layer 102 absorbs and evaporates the heat on the surface of the forehead through the polymeric hydrogel thereof. The polymeric hydrogel is a three-dimensional network polymer material that is hydrophilic but not soluble in water.

In addition, other components except for the polymeric hydrogel in the gel layer 102 will not be defined, which can be either same or not same as the prior art Secondly, the structure of the carrier 20 in the cooling system body will not be defined, as long as the gel layer 102 can be coated on it and the temperature sensing module 30, the touch display module 40 and the control module 50 can be fixed.

For example, the carrier 20 can be e.g. a box body made of a resin material, wherein the gel layer 102 and the temperature sensing module 30 are arranged on a surface of one side of the box body, the touch display module 40 is embedded in the other opposite side of the box body and is exposed, and the control module 50 can be fixed within the box body.

Thirdly, the temperature sensing module 30 can be embedded in the gel layer 102, and can also be located beside the gel layer 102, as long as its sensing surface and a surface of the gel layer 102 away from the carrier 20 are in a same plane.

The surface of the screen of the touch display module 40 and the surface of the carrier away from the gel layer 102 can be in a same plane and can also be not in a same plane, as long as the temperature displayed by it can be seen. On the basis of this, in order to be pleasing to the eye, preferably, the screen of the touch display module 40 and the surface of the carrier 20 away from the gel layer 102 are in a same plane.

In order to be pleasing to the eye, the control module 50 is preferably fixed within the carrier 20.

Fourthly, the temperature sensing module 30 can be a temperature sensor, the sensing surface of which contacts the forehead of the patient so as to obtain the temperature of the forehead. The touch display module 40 can be a liquid crystal display with the touch control function, the screen of which is exactly the display screen of the liquid crystal display. The control module 50 can be a control panel using a Single Chip Micyoco (SCM) and the like as the main control chip.

Fifthly, the skilled person in the art knows that all of the control module 50, the temperature sensing module 30 and the touch display module 40 need to be supplied with power. The power supply module for supplying power can be either fixed within the carrier separately or integrated on the above control panel.

Embodiments of the present disclosure provide a smart cooling system. In the process of using the smart cooling system, the temperature sensing module 30 can obtain the temperature of the forehead of the patient in real time, the control module 50 can display the temperature on the screen of the touch display module 40, so as to learn the body temperature of the patient in the use of the smart cooling system, thereby being capable of learning the effect of the cooling system at any time.

Figure 4:
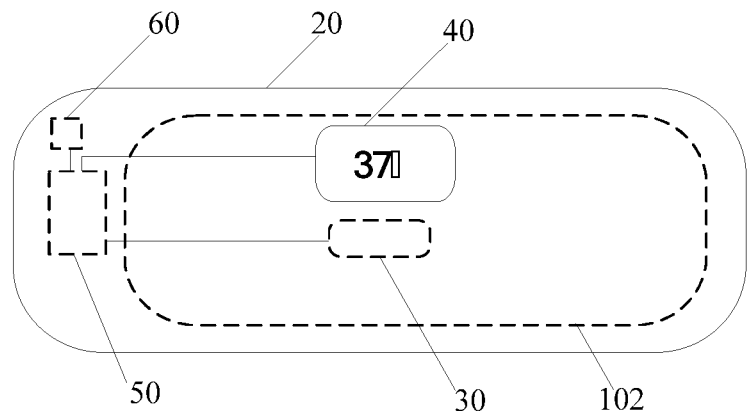
FIG. 4 is a schematic view of a smart cooling system further comprising a storage module on the basis of FIG. 3.

As shown in FIG. 4, the smart cooling system can comprise a storage module 60. The storage module 60 is used for storing the sensed temperature obtained from the temperature sensing module 30 by the control module 50. Here, the storage module 60 can also be integrated on the control panel.

The touch display module 40 can be used for displaying operation control information and obtaining a user instruction based on the operation control information. The operation control information comprises identifications for indicating real time temperature information and temperature curve information. The control module 50 is used for obtaining the real time temperature information or the temperature curve information based on the user instruction and transmitting them to the touch display module 40 so as to enable the touch display module 40 to display.

The above operation control information can be icons displayed on the screen of the touch display module, each icon corresponding to one piece of operation control information. When the user selects a corresponding icon, the operation control information corresponding to this icon will be selected, at the same time, the touch display module 40 will also obtain the user instruction.

Here, the user can realize selection of the corresponding icon through a finger or a stylus pen.

In embodiments of the present disclosure, interaction between the person and the smart cooling system can be realized through the touch display module 40. On the one hand, the temperature can be displayed based on user selection, on the other hand, the user experience can be improved.

When the user instruction indicates that the user selects the real time temperature information, the control module 50 is used for obtaining the sensed temperature from the temperature sensing module 30 and transmitting the sensed temperature to the touch display module 40, so as to enable the touch display module 40 to display the real time temperature.

It should be noted that no matter the user selects an icon corresponding to the real time temperature information or an icon corresponding to the temperature curve information, the control module 50 should obtains the current temperature from the temperature sensing module 30 at a preset interval e.g., 20s. On the basis of this, when the user selects the icon corresponding to the real time temperature information, the touch display module 40 will display the temperature currently obtained by the control module 50, and display different temperatures correspondingly thereafter based on the different temperatures obtained by the control module 50.

When the user instruction indicates that the user selects the temperature curve information, the control module 50 is used for obtaining temperatures within a preset time from the storage module 60, deriving a temperature variation curve based on the temperatures within the preset time, and transmitting the temperature variation curve to the touch display module 40.

That is, no matter the user selects an icon corresponding to the real time temperature information or an icon corresponding to the temperature curve information, the control module 50 should obtain the current temperature from the temperature sensing module 30 continuously at a preset interval e.g. 20s and store it in the storage module 60.

For example, from start use of the smart cooling system, the control module 50 obtains temperatures from the temperature sensing module 30 continuously at an interval of 30s and stores these temperatures in the storage module 60. When the user selects an icon corresponding to the temperature curve information, the control module 50 obtains temperatures stored within the last one hour from the storage module 60, then derives a temperature variation curve based on the temperatures stored within the one hour, and transmits the temperature variation curve to the touch display module 40. When the user selects an icon corresponding to the real time temperature information, the control module 50 transmits the temperature (e.g. 37.5° C.) obtained from the temperature sensing module currently to the touch display module 40, so as to enable the touch display module 40 to display the temperature information of 37.5° C. on its screen.

Figure 5:
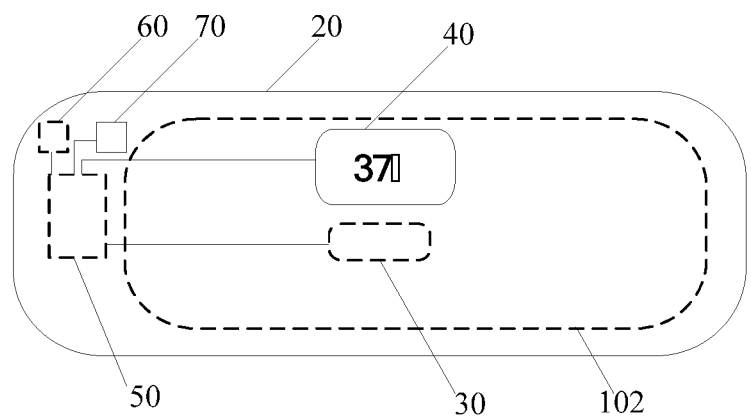
FIG. 5 is a schematic view of a smart cooling system further comprising an alarm module on the basis of FIG. 4.

As shown in FIG. 5, the smart cooling system can comprise an alarm module 70. When the control module 50 determines based on the sensed temperature obtained from the temperature sensing module 30 that the sensed temperature is higher than a preset temperature value, the control module sends an alarm signal to the alarm module 70 so as to enable the alarm module 70 to give an alarm in the form of sound or light.

The alarm module can give an alarm in the form of buzzing or lighting.

It can be learned in time whether the smart cooling system plays a role by giving an alarm by the alarm module when the temperature of the patient is too high, so that other measures can be adopted if necessary to perform cooling, so as to avoid delaying treatment of diseases.

It should be noted that when the alarm module 70 gives an alarm in the form of buzzing, the alarm module 70 can be integrated on the control panel which uses a SCM and the like as the main control chip. When the alarm module 70 gives an alarm in the form of lighting, the alarm module 70 can be either integrated on the control panel or not, however, the alarm module 70 has to be exposed on the front side of the cooling system body.

Figure 6:
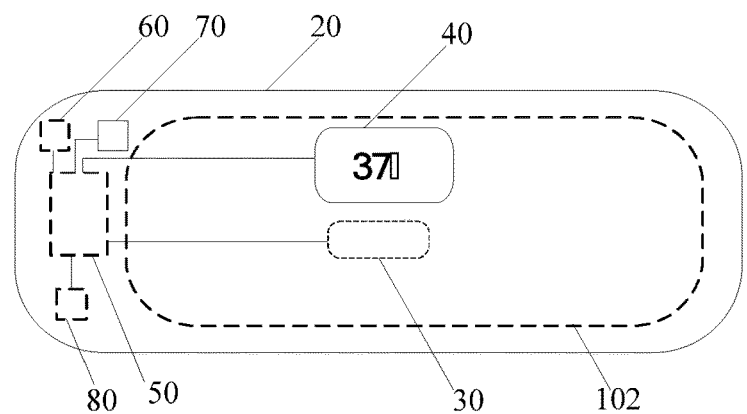
FIG. 6 is a schematic view of a smart cooling system further comprising a communication module on the basis of FIG. 5.

As shown in FIG. 6, the smart cooling system can comprise a communication module 80. The control module 50 transmits the sensed temperature to a mobile terminal through the communication module 80.

The communication module 80 can also be integrated on the control panel which uses a SCM and the like as the main control chip.

The mobile terminal can be a mobile phone, a tablet, a laptop, a desktop computer etc.

The communication module 80 can feed the sensed temperature obtained by the control module 50 to the mobile terminal, so that the parents can monitor the children's condition at any time.

Figure 7:
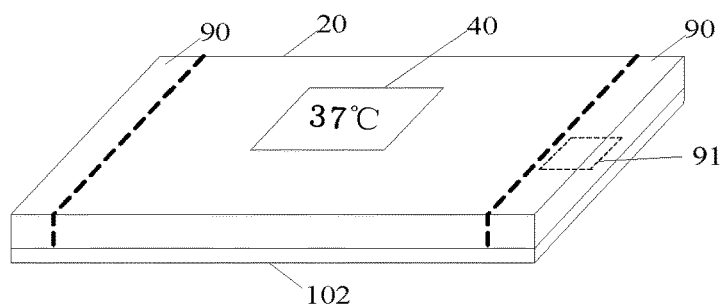
FIG. 7 is a schematic view of a smart cooling system comprising a drugstore device according to embodiments of the present disclosure.

As shown in FIG. 7, the smart cooling system can comprise at least one drugstore device 90 fixed on the carrier 20, in which freshener is stored. The control module 50 can be used for controlling the drugstore device 90 to inject a preset amount of freshener into the gel layer 102 based on the sensed temperature.

The freshener can comprise water, natural cool aromatic plant extractant, and can further comprise natural traditional Chinese medicine composition, skin penetration enhancer etc.

It should be noted that firstly, the structure of the drugstore device 90 and its fixing manner on the carrier 20 will not be defined.

Secondly, one may feel the gel layer 102 very cold when using the cooling system of the prior art because freshener is added herein. The smart cooling system in embodiments of the present disclosure is additionally provided with drugstore devices 90 stored with the freshener, hence, it is easy for the skilled person in the art to understand that less or no freshener can be added to the gel layer 102 in embodiments of the present disclosure relative to the prior art, so that the freshener in the drugstore device 90 will not be added into the gel layer 102 until it is needed.

In embodiments of the present disclosure, after the control module 50 obtains the temperature of the forehead of the patient, it can control the injection amount of the freshener in the drugstore device 90 based on this temperature. For example, when the temperature is high, more freshener can be injected into the gel layer 102, and when the temperature is not too high, less freshener can be injected into the gel layer 102, so that the patient feels very comfortable in the process of using the smart cooling system. The children patients would not have resistance emotion when using the smart cooling system if the gel layer 102 is too cold and the temperature of the patient is not too high.

The drugstore device 90 can have an opening 91 that can be closed. The control module 50 controls the opening 91 to be open based on the sensed temperature so as to enable the freshener in the drugstore device 90 to be injected into the gel layer, and closes the opening 91 when a preset time arrives.

Based on the size of the opening 91 and the time that keeps the opening 91 to be open, the amount of the freshener injected into the gel layer 102 within this time can be learned. On the basis of this, the one-to-one correspondence between the temperature and the time that keeps the opening 91 to be open can be stored in advance. In this way, after the control module 50 obtains the temperature of the forehead of the patient, the opening 91 will be enabled to be in the open state all the time within a time range corresponding to the temperature.

The number of the drugstore devices 90 can be two, and the two drugstore devices 90 are arranged at two opposite ends of the carrier 20 in a detachable manner respectively and are in contact with the gel layer.

The drugstore devices 90 for example can be fixed on the carrier detachably in a pulling manner.

The two drugstore devices 90 are arranged symmetrically. On the one hand, the smart cooling system can look better, on the hand other, more freshener can be stored.

The drugstore devices 90 can be fixed on the carrier 20 in a detachable manner, thus the drugstore devices 90 stored with different fresheners can be selected based on different needs, so as to meet different requirements.

Figure 8:
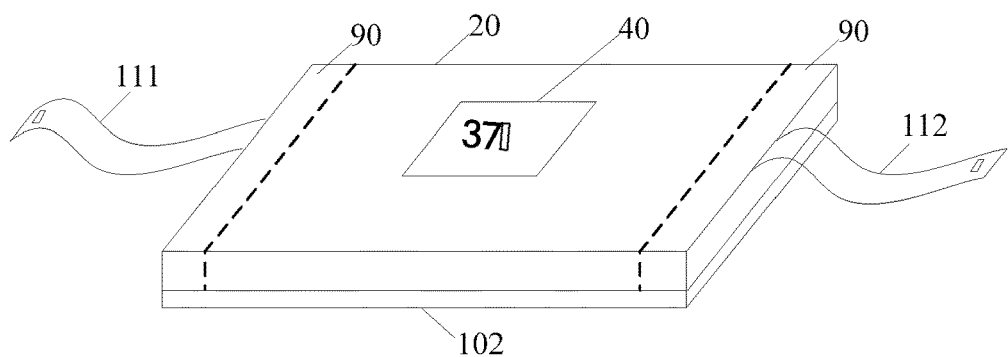
FIG. 8 is a schematic view of a smart cooling system further comprising elastic bands on the basis of FIG. 7.

As shown in FIG. 8, the smart cooling system can comprise a first elastic band 111 and a second elastic band 112 arranged at two opposite ends of the carrier 20 respectively. The first elastic band 111 and the second elastic band 112 are connected in a detachable manner.

When using the smart cooling system, the first elastic band 111 and the second elastic band 112 are connected so as to avoid the smart cooling system dropping off when the patient moves.

What are stated above are only specific implementing modes of the present disclosure, however, the protection scope of the present disclosure is not limited to this. Any modifications or replacements that can be easily conceived by the skilled person in the art familiar with the technical field within the technical scope disclosed by the present disclosure should all be covered within the protection scope of the present disclosure. Therefore, the protection scope of the present disclosure should be subject to the protection scope of the Claims attached.

The invention claimed is:

1. A smart cooling system, comprising: a cooling system body and a temperature sensing module, a touch display module and a control module;
    wherein the cooling system body comprises a carrier being a box body and a gel layer located on the box body; the temperature sensing module, the touch display module and the control module are fixed on the box body;
    a sensing surface of the temperature sensing module is in a same plane as a surface of the gel layer away from the box body, and is used for sensing temperature of a forehead;
    the control module is used for obtaining a sensed temperature and transmitting the sensed temperature to the touch display module;
    a screen of the touch display module is located on a surface of the box body away from the gel layer,
    wherein the smart cooling system further comprises at least one drugstore device fixed on the box body, in which freshener is stored,
    wherein the control module is further used for controlling the drugstore device to inject a preset amount of freshener into the gel layer based on the sensed temperature,
    wherein the drugstore device has an opening that can be closed,
    the control module controls the opening to be open based on the sensed temperature so as to enable the freshener in the drugstore device to be injected into the gel layer, and closes the opening when a preset time arrives.

2. The smart cooling system according to claim 1, further comprising a storage module, wherein the storage module is used for storing the sensed temperature obtained from the temperature sensing module by the control module.

3. The smart cooling system according to claim 2, wherein the touch display module is further used for displaying operation control information and obtaining a user instruction based on the operation control information, the operation control information comprises identifications for indicating real time temperature information and temperature curve information;
    the control module is used for obtaining the real time temperature information or the temperature curve information based on the user instruction and transmitting them to the touch display module.

4. The smart cooling system according to claim 3, wherein when the user instruction indicates that the user selects the real time temperature information, the control module is used for obtaining the sensed temperature from the temperature sensing module and transmitting the sensed temperature to the touch display module; and
    when the user instruction indicates that the user selects the temperature curve information, the control module is used for obtaining temperatures within a preset time from the storage module, deriving a temperature variation curve based on the temperatures within the preset time, and transmitting the temperature variation curve to the touch display module.

5. The smart cooling system according to claim 1, further comprising an alarm module, wherein when the control module determines based on the sensed temperature obtained from the temperature sensing module that the sensed temperature is higher than a preset temperature value, the control module sends an alarm signal to the alarm module so as to enable the alarm module to give an alarm in the form of sound or light.

6. The smart cooling system according to claim 1, further comprising a communication module, wherein the control module transmits the sensed temperature to a mobile terminal through the communication module.

7. The smart cooling system according to claim 1, wherein the number of the drugstore devices is two, and the two drugstore devices are arranged at two opposite ends of the box body in a detachable manner respectively and are in contact with the gel layer.

8. The smart cooling system according to claim 1, further comprising a first elastic band and a second elastic band arranged at two opposite ends of the box body respectively, wherein the first elastic band and the second elastic band are connected to one another in a detachable manner.

* * * * *